United States Patent [19]
Hedaya et al.

[11] 4,130,576
[45] Dec. 19, 1978

[54] METHOD FOR PREPARING ISOCYANATES FROM HALOSILYL CARBAMATES

[75] Inventors: Eddie Hedaya, White Plains; Theodoropulos Spyros, Yorktown Heights, both of N.Y.

[73] Assignee: Union Carbide Corporation, New York, N.Y.

[21] Appl. No.: 862,208

[22] Filed: Dec. 19, 1977

Related U.S. Application Data

[62] Division of Ser. No. 687,160, May 17, 1976, Pat. No. 4,064,151.

[51] Int. Cl.² .......................................... C07C 118/00
[52] U.S. Cl. ................................................. 260/453 P
[58] Field of Search ...................................... 260/453 P

[56] References Cited
PUBLICATIONS

Mironov et al., Russian Journal of General Chemistry, vol. 43, p. 2077 (1973).
Birkofer et al., Angewandte Chemie, vol. 70, p. 404 (1958).
Greber et al., Angewandte Chemie, International Edition, vol. 7, p. 941 (1968).

Primary Examiner—Dolph H. Torrence
Attorney, Agent, or Firm—William R. Moran

[57] ABSTRACT

Isocyanates are prepared directly from amines in a facile process which involves the reaction with halosilyl compounds to form novel halosilyl carbamates. The isocyanate may then be derived from the carbamate intermediate by gentle heating. In accordance with one aspect of the invention, isocyanates can be formed which contain a further reactive functional moiety, such as hydroxyl, amino, mercapto, nitro, sulfonamido, amido, carboxyl or the like.

14 Claims, No Drawings

METHOD FOR PREPARING ISOCYANATES FROM HALOSILYL CARBAMATES

This is a division of our prior U.S. application Ser. No. 678,160 filed May 17, 1976 and now U.S. Pat. No. 4,064,151.

RELATED APPLICATION

Hedaya, Eisenhardt and Theodoropulos, for: Analytical or Clinical Derivatives, Tagged Derivatives and Methods of Analysis Using Such Derivatives, application Ser. No. 687,149, filed May 17, 1976.

BACKGROUND OF THE INVENTION

This invention relates to isocyanates and, more particularly, to a method for synthesizing isocyanates utilizing novel halosilyl carbamates and to the novel halosilyl carbamates.

While other techniques are known, the commercial manufacture of isocyanates is carried out almost exclusively by the reaction of amines with phosgene. The details of processing may vary somewhat with the specific isocyanate being formed, and in particular for aromatic and aliphatic isocyanates, but the general approach is the same. The use of phosgene is undesirable due to its toxicity as well as the care which must be utilized when employing it. In addition, the reaction conditions which are required restrict, to some extent, the type of isocyanates which may be prepared. The problems are multiplied in the manufacture of a diisocyanate, where the simple by-products may be intermolecular, e.g. — a mixed carbamyl chloride/amine hydrochloride, and the urea by-products may be polymeric.

Various silicon derivatives have been employed previously to provide intermediates which break down to yield isocyanates. In *Russian Chemical Reviews*, Vol. 42, p. 669, (1973), a decomposition of an N-silylated carbamic ester under heating to provide isocyanates is disclosed:

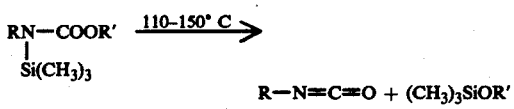

A dehydrative pyrolysis of a silyl carbamate is described in the translation of the *Russian Journal of General Chemistry*, Vol. 43, p. 2077 (1973), UDC 547,245:

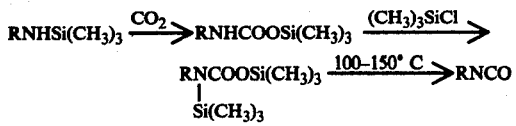

Still further, *Angewandte Chemie*, Vol. 70, p. 404 (1958), shows the formation of a highly substituted isocyanate from N-carbobenzoxy amino acid using trimethylsilyl chloride:

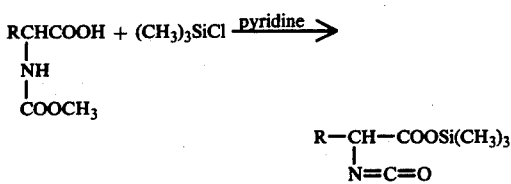

In addition, in *Angewandte Chemie*, International Edition of 1968, at page 941, Vol. 7, there is described the thermal decomposition of nitrogen-substituted trimethylsilylated derivatives of carbamic acid esters, anhydrides, or chlorides. The reaction is shown below, Y referring to the acid derivatives previously mentioned:

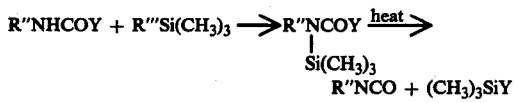

None of the prior work shows the direct, continuous, synthesis of an isocyanate from an amine without the use of phosgene. Still further, in general, the reactions also require a relatively high forcing level of heating to yield the isocyanate.

It is accordingly an object of the present invention to provide a direct, continuous method for preparing isocyanates from amines without employing phosgene.

A further object provides a continuous method for the synthesis of isocyanates from amines which include other reactive, functional groups. A related and more specific object is to provide a method of preparing isocyanates from amines which also include hydroxyl, amino, mercapto, nitro, sulfonamido, amido or carboxylic groups.

Yet another object lies in the provision of preparing halosilyl carbamates.

Another object of this invention is to provide a method of preparing isocyanates in which the isocyanates are synthesized by heating intermediates under mild conditions.

A further object provides a method of preparing isocyanates which can be carried out in a single reaction vessel.

Other objects and advantages of the present invention will become apparent from the following detailed description.

While the invention is susceptible to various modifications and alternative forms, there will herein be described in detail the preferred embodiments. It is to be understood, however, that it is not intended to limit the invention to the specific forms disclosed. On the contrary, it is intended to cover all modifications and alternative forms falling within the spirit and scope of the invention as expressed in the appended claims.

SUMMARY OF THE INVENTION

In general, the present invention is predicated on the discovery that isocyanates may be directly synthesized from amines by forming novel isocyanate intermediates, namely, halosilyl carbamates. In accordance with one procedure, the primary amine utilized is converted to its carbamic acid salt which is then reacted with a silane preferably containing at least two halogen atoms bonded to the silicon to form the halosilyl carbamate. The isocyanate is then formed from the carbamate, by gentle heating. In accordance with an alternative procedure, isocyanates may be formed which can contain a reactive functional group in addition to the isocyanato group. Such reactive functional groups are blocked in the synthesis to prevent polymerization, internal cyclization or the like which might typically otherwise occur. To this end, the carbamic acid salt is first converted to its silylcarbamate which is then converted to the halosilyl carbamate by employing a novel trans-silylation reaction.

The resulting isocyanates may be used for any of the several utilities which are well-known for this type of compound. For example, isocyanates are widely used for forming foams, elastomers and coatings as well as, principally in the case of monofunctional compounds, for the modification of organic compounds. Non-polymer applications for isocyanates lie largely in the field of insecticides, herbicides, and other biologically active products.

DETAILED DESCRIPTION OF THE INVENTION AND PREFERRED EMBODIMENTS

In accordance with the method of the present invention, a primary amine is first reacted with carbon dioxide to form the carbamic acid salt:

$$2 RNH_2 + CO_2 \rightarrow RNHCOO^- N^+H_3R$$

This reaction is well-known and is described in the following literature: Fichter and Becker, *Ber.*, Vol. 44, p. 3041 (1911); Frankel, Neufeld and Katchalski, *Nature*, Vol. 144, p. 832 (1939); Frankel and Katchalski, *J. Amer. Chem. Soc.*, Vol. 65, p. 1670 (1943); Wright and Moore, *J. Amer. Chem. Soc.*, Vol. 70, p. 3865 (1948) and Hayashi, *Bull. Inst. Phys. Chem.* Vol. 11, p. 133 (1932).

Functionally, R can be defined, as is known, as any moiety which as an amine is strong enough as a base to form a carbamate salt with the weak acid, carbon dioxide. Thus, alkyl groups such as methyl, ethyl, butyl, octyl and the like may be employed. Cycloalkyl and halosubstituted alkyl groups may likewise be utilized. In addition, cycloalkyl and halosubstituted cycloalkyl groups such as cyclohexyl, cyclopentyl, 3-chloropropyl and 4-bromocylohexyl groups are useful. Still further, aralkyl groups such as benzyl will also form a carbamate and are within the scope of the present invention.

Other useful groups include alkyl ethers, cyclic ethers such as furan and pyran, thioethers such as thiophenes, cyclic amines such as pyridine and pyrrols, imadazoles, oxazoles, thiazoles, sulfonamides, glycosides, sugars and other carbohydrates and chitin/chitosan.

Still further, aryl and alkaryl groups such as phenyl, tolyl, xylyl and naphthyl may not form carbamates by reaction as an amine; but their amine salts such as lithium anilide, potassium naphthylamine, sodium anthrayl amine and the like may be used since the salts are stronger bases than the parent amine.

The cited literature also discloses useful amines which may be utilized if desired. The disclosure of such literature is incorporated by reference.

It should be further appreciated that the amine reactant selected can be polyfunctional. Thus, diamines, triamines and the like may be employed where polyfunctional isocyanates are desired. Alternatively, when polyfunctional amines are used, one or more of the amino groups can, if desired, be blocked by any of the known techniques in such a fashion as to survive the formation of the isocyanate. After isocyanate formation, the blocked group or groups may then be suitably deblocked, as is known.

A solvent may be employed for the amine to control the temperature and to moderate the rate of reaction; however, if the starting amine is a liquid, a solvent is not absolutely necessary. Either a polar or a nonpolar solvent may be employed. Useful polar solvents include tertiary amines such as, for example, triethylamine. Representative examples of nonpolar solvents include hydrocarbons, halogenated hydrocarbons, ethers, and nitriles. Suitable specific examples include hexane, toluene, tetrahydrofuran and acetonitrile. Solvents containing reactive groups, such as alcohols, are not desirably employed because such solvents would interfere with the reaction.

If a tertiary amine is used as a solvent, this will enter into the reaction. This sequence is shown below with triethylamine:

$$RNH_2 + CO_2 \xrightarrow{(C_2H_5)_3N} RNHCOO^- N^+H(C_2H_5)_3$$

The useful process parameters, as is known in the literature, may vary over a wide range. Stoichiometric amounts will generally be preferred, as deficiencies reduce yields. The use of an excess does not apparantly cause any adverse effects. If employed, the amount of solvent used will generally be dependent upon the reason for utilization. Thus, for example, if a solvent is used for moderating the rate of reaction, the amount of solvent employed will be determined by the extent of moderation desired.

The temperature of the reaction may be carried out over a wide range, varying from about ambient temperatures to about 150° C. However, it is preferred to use lower temperatures in the range of from about 30° to 60° C. to minimize the formation of any side products.

While the reaction has been described in connection with carbon dioxide, it should be appreciated that carbon disulfide or carbon oxysulfide may also be suitably employed. In such cases, isothiocyanates will ultimately be formed. Conceptually, more than one of such compounds could be employed. Also, when a polyamine such as a diamine is utilized, it might be desired to use both carbon dioxide and carbon disulfide. In this fashion, the ultimate product could possess thioisocyanato as well as isocyanato groups. To achieve this type of product, due to differing reactivities, it will generally be desired to initially react the amine with carbon disulfide and then to react the resulting intermediate with carbon dioxide.

As will be appreciated, when either carbon oxysulfide or carbon dioxide are utilized, the criteria for useful amines is the same as has been discussed in connection with carbon dioxide. Thus, any amine may be used if it or its amine salt is strong enough to form the corresponding salt with the oxysulfide or disulfide.

The second step of the procedure involves formation of the novel halosilyl carbamate by reacting the carbamic acid salt with a silane containing at least two halogen atoms bonded to the silicon. This reaction sequence is set forth below:

$$RNHCOO^- N^+H_3R + SiY_2X_2 \rightarrow RNHCOOSiXY_2$$

In the reaction, X defines a halogen atom and may suitably be fluorine, chlorine, bromine or iodine. Y defines either a halogen, hydrogen or an organoic moiety. Conceptually, any organic moiety which allows formation of a halosilyl carbamate and the subsequent conversion to the corresponding isocyanate, as will be described hereinafter, may be suitably utilized. With stoichiometric amounts, the halosilyl carbamates are formed in a substantially quantitative yield. Representative useful organic moieties include lower alkyls containing up to about 10 carbon atoms such as dimethyl, methyl ethyl or methyl propyl. Alicyclic groups such as cyclopentyl, cyclohexyl or cycloheptyl may also be utilized but should contain about 10 carbon atoms or less. Still further, aryl and alkaryl groups containing up to about 10 carbon atoms may be used. Suitable examples include phenyl, tolyl and xylyl. In addition, aralkyl groups containing up to about 10 carbon atoms such as benzyl may also be used. Any of these moieties may be substituted with one or more halogen atoms. It should be understood that the utilization of organic moieties having about 10 carbons or less represents a preference rather than a limitation. Availability and cost will often dictate the particular silane utilized. A further consideration is the ease of conversion to the isocyanate, larger and bulkier organic molecules generally providing a less facile conversion.

It is believed that one halogen atom of the silylating agent serves as an amine acceptor to neutralize the amine from the positive radical of the carbamic acid salt while, of course, the other halogen atom is retained in the reaction product. It is preferred to utilize a silylating agent containing more than two halogen atoms inasmuch as it is believed that the more electron-withdrawing halogen atoms bonded to the silicon, the more facile will be the formation of the desired isocyanate. It is thus preferred to employ tetrachlorosilane. Phenyltrichlorosilane and dimethyldichlorosilane are further representative examples of useful species.

In addition, while chlorosilanes will be typically preferred due to their more ready availability and economy, other electronegative atoms or moieties such as carboethoxy, ethoxy and acetyl groups might likewise be utilized.

The formation of the halosilyl carbamates may suitably be carried out in the same reaction vessel that was utilized in forming the carbamic acid salt; and, indeed, these steps may be carried out simultaneously. The process parameters employed may thus be the same as described herein in connection with the initial step of the reaction.

The resulting halosilyl carbamate, once formed, will slowly generate the isocyanate correponding to the original primary amine. When the reaction mixture is heated, the isocyanate can be distilled from the silicious polymer formed, as shown in the reaction sequence below:

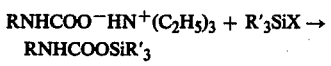

The temperature range utilized for the conversion to the isocyanate may vary widely and will typically range from about ambient to about 150° C. The isocyanate may be recovered by conventional means in yields approaching a quantitative level. Recovery of isocyanates in yields of 80 to 90 percent or even more can generally be achieved. It is unnecessary to isolate the halosilyl carbamate as part of the method; however, if desired, this can be accomplished. The isolated product may be characterized by infrared or nuclear magnetic resonance spectroscopy. While primarily useful in the context of this invention as intermediates in the preparation of isocyanates, the halosilyl carbamates may be utilized in purification of chemical compounds, being used in the same manner as other known silylating agents to, for example, increase the volatility and alter the polarity of the compound being purified.

As can be seen, the halosilyl carbamate contains two oxygen atoms, one of which may be termed the carbonyl oxygen and the other, the ester oxygen. It is believed that this intermediate forms the isocyanate by cleavage of the carbonester oxygen bond of the carbamate with concomitant removal of the hydrogen atom from the nitrogen. It is believed that the electronegative character of the chlorine or other halogen atoms bonded to the silicon atom facilitates this cleavage.

In the alternative procedure, which may be termed the exchange procedure, the carbamic acid salt formed in the first step of the prior procedure described herein is treated with any halosiliane to form the silylcarbamate. This is illustrated below in the instance wherein triethylamine was used as a solvent:

RNHCOO$^-$HN$^+$(C$_2$H$_5$)$_3$ + R'$_3$SiX →
RNHCOOSiR'$_3$

Alternatively, the silylcarbamate could be prepared by insertion of the carbon dioxide by means other than utilizing the carbamic acid salt. In any case, in contrast to the carbamic acid salts which are hygroscopic and may sometimes revert to the amine with the loss of carbon dioxide, the silylcarbamates are generally water-white liquids which can be purified, if desired.

In accordance, with one aspect of the present invention, the silylcarbamate is subjected to a novel trans-silylation reaction to convert the silylcarbamate to a halosilyl carbamate. This reaction is set forth below:

With regard to the reactants, R' of the halosilane represents an organic moiety which may be any of the moieties previously described in connection with the halosilane utilized in the first procedure. Similarly, the halosilane utilized in the trans-silylation reaction may be of the compounds identified in connection with the halosilanes useful in the first procedure.

The haloslyl carbamate, as was described in connection with the initial procedure, will slowly generate the corresponding isocyanate. This may be separated from the exchange reaction mixture by distillation or by filtration, if desired. Silicious polymers will remain in the residue.

The various solvents utilized in the initial procedure as well as the temperature ranges may be also used for the exchange procedure. In the initial procedure, the reaction times will typically vary from about five minutes to about two hours, depending upon the temperatures used, the number and size of substituent groups in the reactants, and the halogen atoms involved. Most typically, the reaction times will fall in the range of from about 15 to about 45 minutes. In the exchange procedure, the reaction times will typically be longer, ranging from about one hour to about six hours.

In both procedures, exact stoichiometric amounts of the reagents are unnecessary, but yields of isocyanates will not be detrimentally affected by employing a slight excess of the silylating agents. Purity of the reactants employed is not critical, except, however, all of the reactants should be dried since water interferes by reacting with both the halogen-containing silylating reactants and with the isocyanate product. Sufficient drying may be achieved by drying the reactants over molecular sieves.

The essential difference between the two procedures resides in the formation of a blocked halosilyl carbamate in the exchange procedure as well as the requirement, in that procedure, of the use of two silylating reagents. Thus, in accordance with one aspect of the present invention, the exchange procedure, which may be carried out in one vessel in a series of steps, can be advantageously employed in situations where the amine contains reactive functionality such as, for example, hydroxyl or carboxyl. The blocked group survives the formation of the isocyanate and may then be suitably deblocked by known techniques when desired. In addition, if desired, the silylcarbamate intermediate may be purified, as by distillation or recrystallization, for applications where a particularly pure isocyanate is desired.

The normal procedure (the initial procedure described), which also may be carried out in one reaction vessel, may prove mor economical due to the fewer reagents and steps needed. Thus, this procedure may be more suitable for synthesizing isocyanates when relatively large quantities are needed.

It should also be appreciated that, while the processes of the present invention have been described in conjunction with silicon reactants, similar reagents of other elements in Group IV or V could likewise be utilized. As representative examples, compounds of tin and germanium could be used. In addition, it is believed that compounds of sulfur, titanium and phosphorus would be useful.

The following Examples are illustrative, but not in limitation, of the present invention.

As used in the Examples appearing hereinafter, the following designations symbols, terms and abbreviations have the indicated meanings:

mol: mole
ml: milliliter
bp: boiling point
g: gram
THF: tetrahydrofuran
ppm: parts per million
m: multiplet
t: triplet
d: doublet
s: singlet
q: quartet
J: coupling constant
eV: electron volts
$R_f$: In thin layer chromatography, the proportion of length of climb of a solution that is reached by a spot characteristic of one of the constituents present.
Hz: Hertz
ir: infrared
nmr: nuclear magnetic resonance

EXAMPLE 1

Two independent experiments were run synthesizing methyl isocyanate, one utilizing chlorobenzene (bp 132° C.) as the solvent, the other using mixed xylenes (bp 139°–144° C.) as the solvent. A 500 ml, three-necked flask was fitted with a Dry Ice/acetone-cooled condenser. About 50g of Dry Ice pieces were placed in the flask and then about 50g of gaseous methylamine was passed in, thus quantitatively forming methylammonium methylcarbamate. After removal of the cooling condenser, the excess Dry Ice was allowed to sublime.

In separate experiments, 21g (0.2 mol) of the carbamic acid salt and 100 ml of each of the above dry solvents were stirred magnetically at room temperature for 30 minutes after 24 ml (0.2 mol) of silicon tetrachloride had been added to the flask which was previously fitted with a distillation column and thermometer. The reaction vessel was then heated over a 30 minute period to 100°–120° C.

In this temperature range, the methyl isocyanate (bp 42° C.) distilled off as rapidly as it was formed. The fraction distilling at 40°–48° C. was in each case separately redistilled resulting in 9g of product in each experiment, a yield of 80%.

EXAMPLES 2–4

The same procedure employed in Example 1 was repeated three times with propylamine substituted for methylamine, using different solvents and stoichiometries. Propyl isocyanate (bp 80°–82° C.) was produced as follows:

| Example | Solvent | Molar Ratio $SiCl_4$/Carbamate | % Yield |
| --- | --- | --- | --- |
| 2a | p-xylene | 1 | 98 |
| 3 | bis-2-methoxy ether | 1 | 70 |
| 4 | bis-2-methoxy ether | 0.5 | 59 |

EXAMPLE 5

Into a 500 ml, three-necked flask fitted with reflux condenser, gas inlet tube, and magnetic stirrer, under a nitrogen atmosphere was charged 19.8g (0.2 mol) of cyclohexylamine. Carbon dioxide from a gas cylinder was allowed to pass in for five minutes to form, quantitatively, 24.2g (0.1 mol) of cyclohexylammonium cyclohexylcarbamate. 150 ml of tetrahydrofuran (THF) dried over 1/16 inch activated molecular sieves and 12.0 ml (0.1 mol) of silicon tetrachloride were then charged into the flask, and the reaction mixture was allowed to stir overnight at room temperature under nitrogen.

The trichlorosilyl carbamate in solution was then separated from the precipitated amine hydrochloride solid by filtration, using a sintered glass funnel. After washing the filter cake with 20 ml of dry THF, the filtrate and washings were concentrated with a rotary evaporator at 30°–40° C. under about 12 torr pressure for about 15 minutes.

The concentrate trichlorosilyl carbamate was decomposed for about 10 minutes at 130°–150° C. at about 12 torr and then distilled. Redistillation gave 12.2g of cyclohexyl isocyanate bp 167°–169° C. (98% yield).

EXAMPLE 6

This Example illustrates the use of triethylamine as a neutralizing reagent for the by-product hydrogen chloride formed.

Into a flask fitted with a reflux condenser, gas inlet tube, and magnetic stirrer, under a nitrogen atmosphere, was charged 50 ml of dry benzene, 45 ml of triethylamine, and 6.0g (0.05 mol) of silicon tetrachloride. In a separate vessel, carbon dioxide gas was bubbled through 22.1g (0.1 mol) of commercial 3-(triethoxysilyl)propylamine dissolved in 20 ml of dry benzene for 10 minutes to form the carbamic acid salt.

The suspension of carbamate was then added dropwise to the reaction flask over the period of 1 hour with stirring at room temperature, and the mixture was allowed to stir for an additional 30 minutes at ambient temperature. The mixed amine hydrochlorides were then filtered off and washed with 30 ml of benzene.

The filtrate and washings upon distillation produced 12g of 3-(triethoxysilyl)propyl isocyanate, bp 75° C. at 0.05 torr, which was a 97% yield.

EXAMPLE 7

This Example illustrates the synthesis of 1,6 hexamethylene diisocyanate by the exchange method.

Into a stirred 500 ml flask under nitrogen, there were charged, in sequence, 11.6g (0.1 mol) of 1,6 hexamethylenediamine in 200 ml of dry THF, 28 ml of triethylamine, and 24 ml (21.6g, 0.2 mol) of trimethylchlorosilane. Carbon dioxide gas was lowly passed into the reaction mixture at reflux for 4 hours.

After stopping the carbon dioxide, 32 ml (42.2g., 0.2 mol) of phenyltrichlorosilane was added; and the heating at reflux was continued for an additional 6 hours. After cooling to room temperature, the reaction mixture was filtered under nitrogen to remove the triethylamine hydrochloride.

The filtrate and washings yielded 13.5g of 1,6 hexamethylene diisocyanate, bp 78°-80° C. at 0.05 torr, an 80% yield.

EXAMPLE 8

This Example illustrates the synthesis of cyclohexyl isocyanate by the exchange method, described in Example 7.

Under nitrogen, 19.8g (0.2 mol) of cyclohexylamine was treated with carbon dioxide gas for 5 minutes to form the carbamic acid salt. 200 ml of dry THF and 14 ml (0.12 mol) of trimethylchlorosilane were then added, and the mixture heated at reflux for 2 hours. The reaction mixture was then cooled, filtrated, and washed as described in Example 7; and the filtrate and washings containing the silylcarbamate were put back into the original flask.

While the mixture was being stirred, 6 ml (0.05 ml) of silicon tetrachloride was added at once by means of a syringe. A white precipitate of trichlorosilylcarbamate formed; and the reaction mixture was the heated at reflux for five hours. The infrared spectrum of the mixture showed disappearance of the carbamate carbonyl band at 5.8μ and appearance of the isocyanate absorption band at 4.45μ.

The reaction mixture was then cooled, concentrated in a rotary evaporator at about 12 torr, and distilled to give 11.8g of cyclohexyl isocyanate, bp 167°-169° C., a 94% conversion.

EXAMPLE 9

This Example demonstrates the synthesis and isolation of the halosilyl carbamate intermediate.

By the method of Example 1, 13.4g of dimethylammonium dimethylcarbamate was made from dimethylamine gas and Dry Ice in a nitrogen atmosphere. The carbamic acid salt was added to 100 ml of dry tetrahydrofuran; and, with stirring at room temperature, 12 ml (10.8g, 0.1 mol) of trimethylchlorosilane was added at once with a syringe. The reaction mixture was than allowed to air for 16 hours.

From this reaction, 16.2 ml (21.1g, 0.1 mol) of trimethylsilyl-N,N-dimethyl carbamate resulted, following removal of dimethylamine hydrochloride by filtration. The filtrate was stirred further at room temperature, and 16.0 ml (0.1 mol) of phenyltrichlorosilane was added to once with a syringe. The reaction mixture was allowed to stir for an additional 16 hours. Concentration of the reaction mixture with a rotary evaporator at 35°-40° C. at about 12 torr yielded, quantitatively, 26g of phenydichlorosilyl-N,N-dimethylcarbamate.

Infrared spectrometry showed disappearance of the alkyl-substituted silylester carbonyl absorption band at 5.92μ and the appearance of the aromatic-substituted silylester carbonyl band at 5.92μ. The nuclear magnetic resonance (nmr) spectrum of this compound in CDCl$_3$ was recorded on a Varian A-60 spectrometer and showed signals at δ 2.83 (m,6,-NCH$_3$) and 7.55 ppm (m,5,aromatic protons).

EXAMPLE 10

The procedure of Example 9, in general, was followed to prepare, from cyclohexylamine, the corresponding halosilylcarbamate.

The carbamic acid salt was first made from the amine and carbon dioxide, as illustrated in Example 8. The salt was then converted to a silylcarbamate by reaction with trimethylchlorosilane, as also described in Example 8.

To 2.1g (0.01 mol) of trimethylsilyl-N-cyclohexylcarbamate dissolved in 200 ml of tetrahydrofuran at room temperature, there was then added 1.6 ml of phenyltrichlorosilane; and the mixture was allowed to stir for 16 hours.

The solvent was then removed at 35°-40° C. in a rotary evaporator under vacuum, forming, in quantitative yield, 3.1g of white, crystalline phenyldichlorosilyl-N-cyclohexylcarbamate. This intermediate, when heated, quickly decomposed to yield cyclohexyl isocyanate.

The intermediate was characterized in its infrared spectrum by a shift in carbonyl absorptions from 5.90 to 5.79μ, showing replacement of an alkyl-substituted silylester carbonyl by an aromatic-substituted silylester carbonyl. This halosilylcarbamate in deuteriochloroform gave an nmr spectrum with absorption bands at δ 1.6 (m, 10, —CH$_2$—), 3.6(m, 1, —CHN) and 7.5 ppm (m, 5, aromatic).

EXAMPLE 11

This Example illustrates the synthesis of an isocynate from an amine bearing a further reactive, functional group: 2-(4'-hydroxyphenyl)ethylamine (trivially-tyramine).

Into a 250 ml, three-necked flask fitted with a reflux condenser, gas inlet tube and magnetic stirrer and kept under a positive pressure of dry nitrogen, there was charged 100 ml of dry tetrahydrofuran, 1.4g (0.01 mol) of tyramine and 5.0 ml of triethylamine. 3.0 ml of trimethylchlorosilane was then added at ambient temperature, dropwise and with stirring over a period of 30 minutes. Carbon dioxide was thereafter slowly bubbled into the reaction mixture, via a syringe needle for 4 hours while the mixture was allowed to reflux for the same period. Introduction of carbon dioxide was then terminated, and 1.5 ml of silicon tetrachloride was added slowly using a syringe. After 30 minutes of additional heating, the reaction mixture was allowed to cool, and triethylamine hydrochloride was removed by filtration. The solvent was then removed at 35° C. in vacuo (12 torr), and the resulting oil distilled at 88°-90° C. (0.05 torr) to give 2-(4'-trimethylsiloxyphenyl)ethyl isocyanate as a colorless liquid.

The infrared spectrum of this novel compound showed absorption bands at 3.39, 4.41, 6.17 and 6.58μ. The nmr spectrum in CDCl$_3$ showed absorptions at δ7.08 and 6.77 (A₂B₂q, 4, J = 8.4 Hz, aromatic 3'-, 5'- and 2'-, 6'-protons, respectively), 3.43 (t, 2, J = 6.6 Hz, —CH₂CH₂—N), 2.79 (t, 2, J = 6.6 Hz, —CH₂CH₂N) and 0.25 ppm (s, 9, —OSi(CH₃)₃). The mass spectrum showed a molecular ion at m/e 235, and additional peaks at 179, 163, 107 and 73, and a metastable peak at 163.3.

EXAMPLE 12

This Example demonstrates the synthesis of methyl-2-isocyanato-3-(4'-trimethylsiloxyphenyl)propionate (trivially-blocked L-tyrosine methyl ester isocyanate).

Through a stirred mixture of 9.75g (0.05 mol) of L-tyrosine methyl ester, suspended in 200 ml of dry tetrahydrofuran and 45 ml (0.30 mol) of triethylamine, there was bubbled a stream of dry carbon dioxide. After 30 minutes, 20 ml (0.16 mol) of trimethylchlorosilane was added slowly; and the mixture, with carbon dioxide continuously bubbling through, was allowed to reflux for 4 hours. The reaction mixture was then allowed to cool to room temperature, the carbon dioxide bubbling discontinued, 8.5g (6.0 ml, 10.05 mol) of silicon tetrachloride slowly added, and the mixture allowed to stir at ambient temperature for 20 minutes.

The mixture was thereafter allowed to reflux for one hour, then cooled to ambient temperature, and 50 ml of tert-butyl alcohol was added. The mixture was then allowed to stir at ambient temperature for 30 minutes. The mixture was then filtered under nitrogen, the filter cake washed with 30 ml of dry THF, and the combined filtrates concentrated in vacuo and distilled using a short-path column.

The fraction collected at 100°–145° C. (0.05 mm) was redistilled to give 5.8g (39%) of methyl-2-isocyanato-3-(4'-trimethylsiloxyphenyl)propionate as a viscous, colorless oil: bp 139°–40° C. (0.1 mm); ir (neat smear) 3.38, 4.45 (N═C═O), 5.73 (ester C═O), 6.22, 6.64, 10.9 and 11.8μ; nmr (CCl₄) δ 7.00 and 6.70 (A₂B₂q, 4, J = 8.6 Hz, aromatic 3'-, 5'- and 2'-, 6'-protons, respectively), 4.10 (t, 1, J = 6.0 Hz, —CH₂—CH—), 3.66 (s, 3, —OCH₃), 2.91 (d, 2, J = 6.0 Hz, —CH₂—CH—) and 0.22 ppm (s, 9, (CH₃)₃Si—); mass spectrum (70eV) m/e (rel intensity) 293 (5), 278 (1.5), 250 (1), 234 (2.5), 218 (0.75), 179 (100), 163 (2.3), 149 (2), 107 (2), and 73 (40).

EXAMPLE 13

This Example illustrates the synthesis of methyl-2-isocyanato-3-(4'-tert-butyldimethylsiloxyphenyl) propionate.

The procedure of Examples 12 and 13 was, in general, followed. Into 100 ml of dry tetrahydrofuran there was added 8.0g (0.04 mol) of L-tyrosine methyl ester. A slow stream of dry carbon dioxide gas was bubbled into the stirred reaction mixture for 30 minutes while 50 ml of triethylamine was added dropwise. 15g (0.1 mol) of tert-butyldimethylchlorosilane was then added, and the reaction mixture was heated at reflux for 4 hours. After cooling, 8.5g (6.0 ml, 0.05 mol) of silicon tetrachloride was added, whereupon the reaction mixture was stirred for 30 minutes and heated at reflux for 1 additional hour. 50 ml of tert-butyl alcohol was then added to decompose any silylchlorides and stirring was continued for an additional 30 minutes.

After filtration, washing, and concentration of the reaction mixture as described in the prior Examples, 2.7g (20 percent yield) of colorless isocyanate boiling at 180° C. (0.5 torr) was isolated. Infrared absorption peaks (smear) were found at 3.38, 4.44, 5.71, 6.17 and 6.54μ. The nmr spectrum (CDCl₃) was characterized by signals at δ 7.83 and 6.83 (A₂B₂q, 4 J = 8.6 Hz, aromatic 3'-, 5'- and 2'-, 6'-protons, respectively), 4.26 (t, 1, J = 6.0 Hz, —CH₂CH), 3.83 (s, 3, —OCH₃), 3.08 (d, 2, J = 6.0 Hz, —CH₂CH—), 1.03 (s, 9, —C(CH₃)₃) and 0.26 ppm (s, 6, —Si(CH₃)₂). The mass spectrum showed peaks at m/e 335, 278, 250, 236, 221, 205, 172, 73 and 57.

EXAMPLE 14

This Example illustrates the synthesis of 2-trimethylsiloxyethyl isocyanate by the exchange method described in Example 7.

Under nitrogen, 6.1g (0.1 mol) of ethanolamine and 100 ml of triethylamine dissolved in 100 ml of dry THF was treated with carbon dioxide gas to form the carbamic acid salt. 24 ml (0.2 mol) of trimethylchlorosilane was then added with a syringe and the mixture heated at reflux for 2 hours. At this point, the carbon dioxide gas treatment was discontinued and the reaction mixture was then cooled, filtered and washed as described in Example 7; and the filtrate and washings containing the silylcarbamate were put back into the original flask.

While the mixture was being stirred, 12 ml (0.05 mol) of silicon tetrachloride was added dropwise over a period of 15 minutes. The reaction mixture was then allowed to stir overnight, filtered, concentrated under vacuum and distilled to give 2-trimethylsiloxyethyl isocyanate, bp 27'–29° C. at 0.02 millimeters.

The ir (neat smear) showed 3.42, 4.42 (N═C═C), 8.0 (TMS), 9.0, 10.67 and 11.95μ. The nmr spectrum in CDCl₃ showed absorptions at δ 3.71 (t, 2, J = 5.0 Hz), 3.28 (t, 2, J = 5.0 Hz), and 0.16 ppm (s, 9, Si—(CH₃)₃.

What is claimed is:

1. A process of preparing isocyanates in a liquid phase reaction from primary amines which comprises reacting a primary amine with carbon dioxide to form the corresponding carbamic acid salt, reacting the carbamic acid salt to form a halosilyl carbamate having the formula:

wherein R is the organic moiety of the primary amine, X is halogen and Y is a member selected from the group consisting of halogen, hydrogen, lower alkyl, alicyclics, aryl, alkaryl and aralkyl, each having no more than about 10 carbon atoms, and heating the halosilyl carbamate to a temperature and for a time sufficient to yield the isocyanate.

2. The process of claim 1 wherein the halosilyl carbamate is formed from the carbamic acid salt by reacting the carbamic acid salt with a halosilane having the formula:

wherein X is halogen and Y is a member selected from the group consisting of halogen, hydrogen, lower alkyl, alicyclics, aryl, alkaryl and aralkyl, each having no more than about 10 carbon atoms.

3. The process of claim 1 wherein the halosilyl carbamate is formed from the carbamic acid salt by reacting the carbamic acid salt with a monohalosilane to form the silyl carbamate and then trans-silylating the silyl carbamate by reaction with a halosilane having the formula:

wherein X is halogen and Y is a member selected from the group consisting of halogen, hydrogen, lower alkyl, alicyclics, aryl, alkaryl, and aralkyl, each having no more than about 10 carbon atoms.

4. The process of claim 1 wherein the process is carried out at a temperature in the range of from ambient to about 150° C.

5. The process of claim 1 wherein the process is carried out at a temperature in the range of from about 30° C. to about 60° C.

6. The process of claim 1 wherein the process is carried out in the presence of a tertiary amine as a solvent.

7. The process of claim 6 wherein the tertiary amine is triethylamine.

8. The process of claim 2 wherein the halosilane is a chlorosilane.

9. The process of claim 2 wherein the halosilane is a member selected from the group consisting of silicon tetrachloride, phenyltrichlorosilane and dimethyldichlorosilane.

10. The process of claim 2 wherein the halosilane is silicon tetrachloride.

11. The process of claim 3 wherein the halosilane is a chlorosilane.

12. The process of claim 3 wherein the halosilane is a member selected from the group consisting of silicon tetrachloride, phenyltrichlorosilane and dimethyldichlorosilane.

13. The process of claim 3 wherein the halosilane is silicon tetrachloride.

14. The process of claim 1 wherein the organic radical of the primary amine contains at least one reactive, functional group.

* * * * *